United States Patent
Landgraf et al.

[11] Patent Number: 5,888,545
[45] Date of Patent: Mar. 30, 1999

[54] CARBAMAZEPINE MEDICAMENT WITH RETARDED ACTIVE SUBSTANCE RELEASE

[75] Inventors: Karl-Friedrich Landgraf; Sabine Reiss, both of Dresden; Eberhard Schubert, Radebeul, all of Germany

[73] Assignee: Arzneimittelwerk Dresden GmbH, Radebeul, Germany

[21] Appl. No.: 776,266

[22] PCT Filed: Jun. 22, 1995

[86] PCT No.: PCT/DE95/00805

§ 371 Date: Apr. 24, 1997

§ 102(e) Date: Apr. 24, 1997

[87] PCT Pub. No.: WO96/01112

PCT Pub. Date: Jan. 18, 1996

[30] Foreign Application Priority Data

Jul. 1, 1994 [DE] Germany ............ 44 23 078.8

[51] Int. Cl.⁶ .................................................. A61K 9/22
[52] U.S. Cl. .................. 424/468; 424/464; 424/474; 424/487; 424/497; 427/215; 427/216; 427/213; 427/213.36; 427/212; 514/960; 514/962; 514/963; 514/964
[58] Field of Search ........................ 424/464, 468, 424/474, 487, 497; 427/2.15, 2.16, 213, 213.36, 212; 514/964, 960, 962, 963

[56] References Cited

U.S. PATENT DOCUMENTS 4,572,833  2/1986  Pedersen et al. .................. 424/20

FOREIGN PATENT DOCUMENTS

| 080 341 | 6/1983 | European Pat. Off. . |
| 388 954 | 9/1990 | European Pat. Off. . |
| 37 25 824 | 2/1988 | Germany . |
| 2 122 490 | 1/1984 | United Kingdom . |

OTHER PUBLICATIONS

Embase Abstract No. 93329228 & Pharm.Ind. 1993, Band 55, No. 10, S.940–947.

Drug Development and Industrial Pharmacy, vol. 17, No. 13, 1991, pp. 1753–1764, P. Guinchedl et al:, "Carbarnazepine modified release dosage form".

Primary Examiner—Thurman K. Page
Assistant Examiner—Lakshmi Channavajjala
Attorney, Agent, or Firm—Pillsbury Madison & Sutro LLP

[57] ABSTRACT

An oral administration carbamazepine medicament with a retarded active substance release is disclosed. An aqueous plasticised polymer dispersion is applied on carbamazepine crystals without causing formation of carbamazepine dihydrate. The carbamazepine crystals with their aqueous coating may be mixed with appropriate auxiliarly substances, shaped into divisible tablets or filled into capsules.

1 Claim, 2 Drawing Sheets

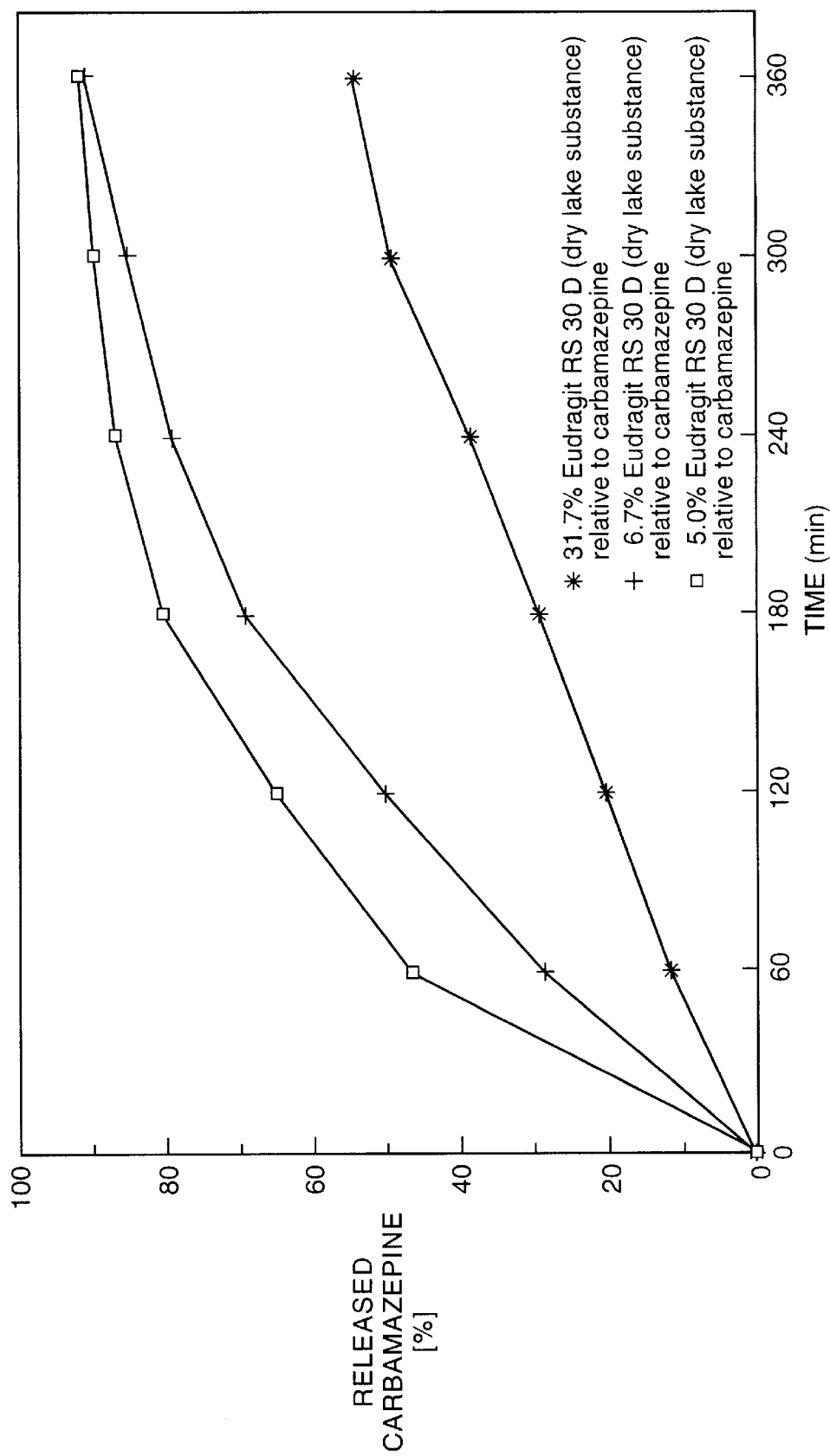

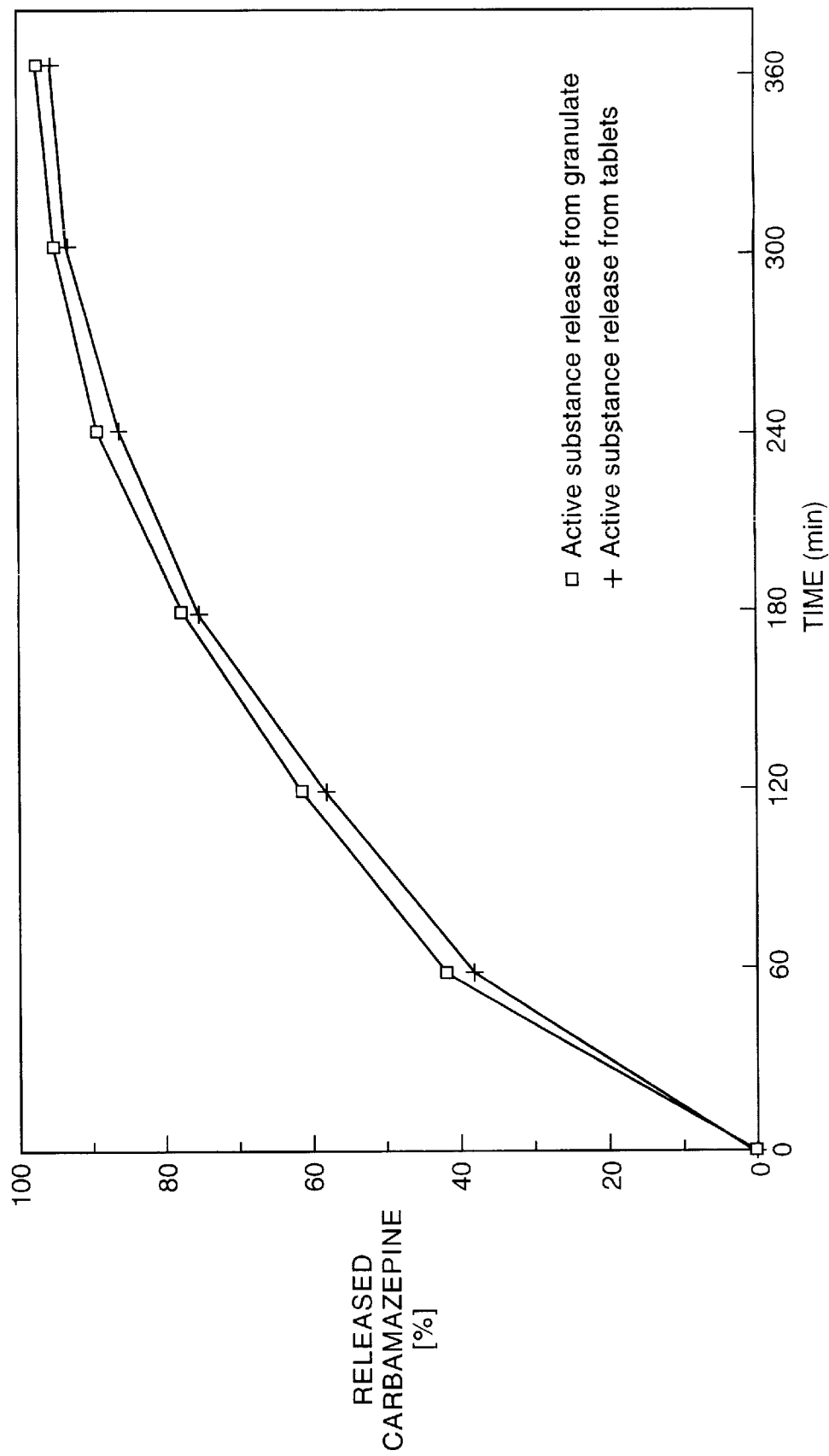

CARBAMAZEPINE MEDICAMENT WITH RETARDED ACTIVE SUBSTANCE RELEASE

This application is based on German Patent Application DE 4423078.8 filed Jul. 1, 1994 and PCT/DE95/00805, filed Jun. 22, 1995, the contents of which are incorporated hereinto by reference.

BACKGROUND OF THE INVENTION

The invention is relative to an orally applicable carbamazepine medicament with retarded active substance release. Carbamazepine, a 5 H-dibenz(b,f)azepine-5-carboxamide, is used in particular as an antiepileptic. Commercial forms of administration are tablets with 200 mg active substance, delayed-action tablets with 200 to 600 mg active substance and syrups.

It is known that carbamazepine very rapidly forms a dihydrate upon contact with water. This dihydrate is present in a crystalline form as needles which can grow up to a particle size of 500 µm. This has a negative effect on the further processing, especially when developing retarding coatings. The known methods of production therefore do not use aqueous media and prefer to use organic solvents.

The retarding of an active substance can take place in various ways. DE patent 23 77 520 describes a formulation for carbamazepine in which the active substance is mixed with customary inactive tableting ingredients and pressed to a core or filled into capsules. The core or the capsule is coated with a methacrylic acid-methacrylic acid methylester mixture dissolved in isopropanol which mixture contains acetyltributylcitrate as softener. In this manner the forming of dihydrate by carbamazepine is prevented by the use of an organic solvent.

DE patents 38 68 077 and 37 25 824 claim a carbamazepine inactive ingredient composition containing a protective colloid which inhibits the crystalline growth of carbamazepine in the presence of water. The carbamazepine-containing core is coated in them with an organic solvent of cellulose acetate. A passage in the form of a perforation is placed in the film in a suitable manner.

The methods of producing these formulations have the disadvantage that the work must be carried out with organic solvents, which impacts the environment and signifies great effort and expense.

Furthermore, these medicaments produced as described above (tablets and capsules) are not divisible, since the casing is damaged in a division and the retarding action is lost therewith. Thus, the dosing possibilities are limited.

In addition, preparations (tablets) are known which do not lose their retarding action in a division or a disintegration into individual particles in liquids outside of or within the gastrointestinal tract. Pharm. Ind. 55, No. 10 (1993) pp. 940–947 describes compact oral preparations in which individual particles are coated with aqueous dispersions of copolymers of methacrylic acid and methylmethacrylic acid esters and pressed to tablets. The addition of 25–50% inactive ingredients brings about a more rapid decomposition of the tablets. The addition of a softener makes it possible to considerably increase the elongation at break of the coating and assures the mechanical stability. The coating of paracetamol-, potassium chloride- and acetylsalicylic acid active substance crystals, theophylline granulate and indomedacine and theophylline pellets are cited in this connection.

The present invention has the problem of making available a carbamazepine medicament in which, in spite of the use of water as solvent or dispersing agent, the crystal growth associated with the formation of dihydrate by the carbamazepine is prevented and the release of the carbamazepine is sufficiently retarded.

SUMMARY OF THE INVENTION

The invention solves the problem in that film formers are applied in combination with a softener as aqueous solution and/or dispersion onto carbamazepine. The coated carbamazepine can optionally be mixed with further inactive ingredients and pressed to tablets or filled into capsules.

DETAILED DESCRIPTION OF THE INVENTION

Polymethacrylate dispersions are used as film formers for the retarding of carbamazepine. The following are preferred:

A mixture of polyethylacrylate and polymethylmethacrylate in a ratio of 2:1 (Eudragit® NE 30 D), A mixture of polyethylacrylate, polymethylmethacrylate and polytrimethylammonioethylmethacrylate chloride in a mixture of 1:2:0.1 (Eudragit® RS 30 D) or The previously cited mixture in a ratio of 1:2:0.2 (Eudragit® RL 30 D).

Potential water-soluble softeners are e.g. glycerol triacetate or triethylcitrate. They are used in a ratio of dry lake substance to softener such as 1:0.05 to 1:0.25, preferably 1:0.15 to 1:0.22.

BRIEF DESCRIPTION OF THE DRAWINGS

FIG. 1 illustrates graphically the release curves for different ratios of carbamazepine to film former.

FIG. 2 illustrates graphically the retardation rate of the dissolution rate for carbamazepine and coated carbamazepine according to the invention.

The ratio of film former to carbamazepine is a function of the retarding effect to be achieved and is 1:0.03 to 1:0.5. In particular, a ratio of carbamazepine to film former of 1:0.05 to 1:0.1 is used, but preferably 1:0.05 to 1:0.08.

The release curves for such different ratios of carbamazepine to film former are shown in FIG. 1. The Dissolutions test of USP XXII for carbamazepine was used as method (medium: Water with 1% sodium dodecylsylfate additive).

Surprisingly, the composition of the carbamazepine medicament in accordance with the invention was able to prevent the dihydrate formation which occurs spontaneously, as is known, when carbamazepine makes contact with water and with is associated with a needle-like growth of crystals and thus to prevent poor processability.

The film former combined with a softener is advantageously sprayed on as aqueous solution and/or dispersion in a fluid-bed granulator. In addition, in order to prevent the adhering of the coated particles separating agents can be added to the dispersion and/or sprayed on subsequently in the fluid bed as separate suspension. For example, talcum is applied in a concentration ratio of dry lake substance to separating agent such as 1:0.4 to 1:1, preferably 1:0.45 to 1:0.55.

Further galenic inactive ingredients can be mixed in with the coated carbamazepine crystals in a known manner. the mixtures produced in this manner or even the coated crystals can then be filled into hard gelatine capsules or pressed to divisible tablets. The mechanical stressing of the individual particles associated with the cited further processing of the coated carbamazepine, especially in tabletting, does not damage the film coating.

The final medicament displays the same retardation of the dissolution rate, tested according to the method of USP XXII for carbamazepine, as the coated carbamazepine (FIG. 2).

The method of the invention is explained in detail using the exemplary embodiments:

EXAMPLE 1

A suspension is produced from 2.23 kg Eudragit RS 30 D, 135 g glycerol triacetate dissolved in 2.35 l water and 325 g talcum suspended in 1 l water. The suspension is sprayed on 10 kg carbamazepine in a WSG 15 fluid-bed granulator (Glatt company). Then, a suspension of 625 g talcum in 2 l water is sprayed on. The granulate obtained in this manner is mixed with 914 g microcrystalline cellulose, 653 g insoluble polyvidone, 70 g highly disperse silicon dioxide and 35 g magnesium stearate. The mixture is pressed to tablets with an active-substance content of 200, 400 or 600 mg carbamazepine or the corresponding amount of granulate is filled into capsules of size 1.

EXAMPLE 2

A suspension is produced from 340 g Eudragit RS 30 D, 20.4 g triethylcitrate dissolved in 0.3 l water and 40 g talcum suspended in 0.1 water. The suspension is sprayed on 1 kg carbamazepine in a GPCG 1 fluid-bed granulator (Glatt company) at a product temperature of 27°–30° C. The granulate obtained in this manner is mixed with 65 g microcrystalline cellulose, 65 g insoluble polyvidone, 7 g highly disperse silicon dioxide and 3.5 g magnesium stearate. The mixture is pressed to tablets with an active-substance content of 200, 400 or 600 mg carbamazepine or the corresponding amount of granulate is filled into capsules of size 1.

EXAMPLE 3

A suspension is produced from 29 g Eudragit NE 30 D, 1.3 g glycerol triacetate dissolved in 0.03 l water and 9 g talcum suspended in 0.03 water. The suspension is sprayed on 250 g carbamazepine in a Glatt UNI fluid-bed granulator at a product temperature of 27°–30° C. The granulate obtained in this manner is mixed with 16 g microcrystalline cellulose, 16 g insoluble polyvidone, 2 g highly disperse silicon dioxide and 1 g magnesium stearate. The mixture is pressed to tablets with an active-substance content of 200, 400 or 600 mg carbamazepine or the corresponding amount of granulate is filled into capsules of size 1.

We claim:

1. A method of producing a carbamazepine medicament with retarded active substance release comprising spraying film formers in combination with softener as an aqueous solution or an aqueous dispersion onto carbamazepine in a fluid-bed granulator to form a coated carbamazepine and filling the coated carbamazepine without further inactive ingredients into capsules.

* * * * *